US00PP23720P3

(12) United States Plant Patent

Zaiger et al.

(10) Patent No.: US PP23,720 P3

(45) Date of Patent: Jul. 9, 2013

(54) INTERSPECIFIC TREE NAMED: 'FLAVOR BLAST'

(50) Latin Name: **Interspecific *Prunus* sp.**
Varietal Denomination: FLAVOR BLAST

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 72 days.

(21) Appl. No.: 13/374,091

(22) Filed: Dec. 12, 2011

(65) Prior Publication Data

US 2013/0152249 P1 Jun. 13, 2013

(51) Int. Cl.
*A01H 5/00* (2006.01)

(52) U.S. Cl.
USPC ..... Plt./180

(58) Field of Classification Search
USPC ..... Plt./180
See application file for complete search history.

*Primary Examiner* — Annette Para

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Vigorous, upright tree growth.
2. Heavy and regular bearer of fruit.
3. Fruit with very firm flesh.
4. Fruit with excellent eating quality.
5. Fruit with an average Brix of 26° and a good balance between acid and sugar.
6. Fruit with good handling and shipping quality.

1 Drawing Sheet

Botanical classification: Interspecific *Prunus* sp.
Variety denomination: 'FLAVOR BLAST'.

BACKGROUND OF THE VARIETY

1. Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

2. Prior Varieties

Among the existing varieties of cherries, plums and interspecifics, which are known to us, and mentioned herein, 'Minnie Royal' Cherry (U.S. Plant Pat. No. 12,942), the proprietary (non-patented) interspecific seedlings '319LU21', '178LM220', 'Honey Punch' Interspecific (U.S. Plant Pat. No. 19,596), the proprietary (non-patented) plum '37ED370' and our (non-patented) proprietary cherry '5GK125'.

STATEMENT REGARDING FEDERALLY SPONSORED RESEARCH AND DEVELOPMENT

Not applicable.

ORIGIN OF THE VARIETY

The new and distinct interspecific tree originated by us from crosses between the following species [(*Prunus salicina*×*Prunus avium*)×*Prunus avium*]. The present variety was selected as an open pollinated seedling from seed of our proprietary interspecific '319LU21' (non-patented). The seed parent originated as a first generation cross between our proprietary interspecific '178LM220' and 'Minnie Royal' Cherry (U.S. Plant Pat. No. 12,942). The interspecific seedling '178LM220' (non-patented) originated as a cross between our proprietary plum seedling '37ED370' (non-patented) and our proprietary cherry seedling '5GK125' (non-patented). We grew a large number of these seedlings and under close and careful observation the present seedling exhibited desirable fruit and tree characteristics and was selected in 2006 for additional asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new and distinct variety of interspecific tree which includes [(Plum×Cherry)×Cherry] in its parentage is of large size, vigorous upright growth and a productive and regular bearer of medium size fruit with very firm flesh and excellent eating quality. The fruit is further characterized by holding firm on the tree 2 weeks after maturity (shipping ripe), having high Brix and good storage and shipping quality. In comparison to its immediate parent (319LU21), the fruit of the new interspecific variety has firmer flesh, skin color is red and yellow compared to solid red and is approximately 24 days later in maturity. In comparison to the commercial interspecific variety 'Honey Punch' (U.S. Plant Pat. No. 19,596) the fruit of the new variety has bright red skin compared to dark red, yellow flesh compared to red flesh and is approximately 12 days later in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 6 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 6 year old specimens grown near Modesto, Calif., with color in accordance with Munsell Book of Color.

Tree:

*Size*.—Large, pruned to 3 to 3.5 meters in height and width for economical harvesting of fruit. Varies with different cultural practices.

*Vigor*.—Vigorous, tree growth of approximately 1.5 to 2 meters the first growing season. Varies with cultural practices, soil type, fertility and climatic conditions.

*Form*.—Upright, usually pruned to vase shape.

*Branching habit*.—Upright, crotch angle approximately 35°, increase with heavy crop load.

*Productivity*.—Productive, thinning and spacing of fruit desirable for market size.

*Bearer*.—Regular, adequate fruit set 4 consecutive years. No alternate bearing observed.

*Fertility*.—Self sterile, pollinator required.

*Density*.—Medium dense, usually pruned to vase shape to increase sunlight and air movement to center of tree to enhance fruit color and health of fruit spurs.

*Hardiness*.—Hardy in all stone fruit growing areas of California. Tree growing in USDA Hardiness Zone 9. Winter chilling requirement is approximately 700 hours at or below 45° F.

Trunk:

*Size*.—Medium to large. Average circumference 61.5 cm at 20.3 cm above ground level on a 6 year old tree.

*Stocky*.—Medium stocky.

*Texture*.—Medium shaggy, becomes rougher with age.

*Color*.—Varies from 2.5Y 5/4 to 7.5Y 4/2.

Branches:

*Size*.—Medium. Average circumference 11.9 cm at 1.2 meters above ground. Crotch angle approximately 35°, increase with heavy crop load.

*Surface texture*.—New growth relatively smooth. Mature growth medium rough, roughness increase with age.

*Lenticels*.—Size — medium. Average number 83 in a 25.8 sq cm area. Average length 2.5 mm. Average width 0.9 mm. Color varies from 7.5YR 7/8 to 7.5YR 6/10.

*Color*.—New growth varies from 5GY 6/6 to 5GY 5/8. Old growth varies from 7.5YR 2/4 to 10YR 2/2, varies with age of growth.

Leaves:

*Size*.—Medium. Average length 96.5 mm. Average width 53.3 mm.

*Form*.—Oblanceolate.

*Apex*.—Acuminate.

*Base*.—Cuneate.

*Margin*.—Serrate.

*Thickness*.—Medium.

*Surface texture*.—Upper surface relatively smooth, slight indentations over midrib and leaf veins. Lower surface relatively smooth except for small ridges created by midrib and pinnate venation. Both upper and lower surfaces glabrous.

*Petiole*.—Average length 11.4 mm. Average width 1.9 mm. Longitudinally grooved. Pubescence present. Color varies from 5GY 6/6 to 7.5R 3/4 where exposed to the sun.

*Glands*.—Type — globose. Size — small. Average length 0.7 mm. Average diameter 0.4 mm. Number varies 1 to 3, average number 2. Located primarily on the lower portion of the leaf blade and on the upper portion of the petiole. Color 2.5GY 7/6.

*Stipules*.—Average number 2. Average length 5.3 mm. Edges — serrate. Color varies from 5GY 6/6 with 7.5R 3/4 on edges.

*Color*.—Upper surface 5GY 3/4 to 5GY 2/2. Lower surface 7.5GY 4/4 to 5GY 4/4. Midvein color varies from 5GY 7/6 to 5GY 6/6.

Flower buds:

*Size*.—Small to medium. Average length 8.8 mm. Average diameter 4.5 mm.

*Hardiness*.—Hardy with respect to California winters.

*Form*.—Conical, becomes elongated just before opening.

*Pedicel*.—Average length 4.9 mm. Average width 0.7 mm. Color varies from 2.5GY 7/8 to 2.5GY 6/8.

*Color*.—N 9.5/(white).

*Number of buds per spur*.—Average number 10, varies from 9 to 13. Varies with age of spur.

Flowers:

*Blooming period*.—Date of First Bloom Feb. 27, 2011. Date of Petal Fall Mar. 7, 2011, varies with climatic conditions.

*Size*.—Medium. Average height 11.6 mm. Average diameter 19.4 mm.

*Petals*.—Size — medium. Number — normally 5, alternately arranged to sepals. Average length 9.3 mm. Average width 7.8 mm. Form — globose, slightly narrows at point of attachment. Margin — sinuate. Color — N 9.5/(white). Both surfaces glabrous.

*Sepals*.—Normally 5, alternately arranged to petals. Size — small to medium. Average length 3.1 mm. Average width 2.7 mm. Form — triangular, apex rounded. Margin — entire. Color — upper surface varies from 5GY 6/8 to 2.5GY 6/8. Lower surface varies from 2.5GY 6/8 to 5R 3/8. Both upper and lower surfaces glabrous.

*Stamens*.—Average number per flower 39. Average filament length 8.6 mm. Filament color N 9.5/(white). Anther color varies from 2.5Y 5/8 to 10YR 4/6.

*Pollen*.—Self sterile, pollinator required. Color varies from 2.5Y 7/12 to 7.5Y 7/10.

*Pistil*.—Normally one. Surface — glabrous. Average length 8.3 mm. Stigma height approximately 2.1 mm below anthers. Color varies from 5Y 8/10 to 10Y 7/8.

*Fragrance*.—Heavy aroma.

*Color*.—N 9.5/(white).

*Number flowers per flower bud*.—Average number 2, varies from 1 to 3.

*Pedicel*.—Average length 5.8 mm. Average width 0.9 mm. Color varies from 2.5GY 6/6 to 2.5GY 7/8. Surface — glabrous.

Fruit:

*Maturity when described*.—Firm ripe.

*Date of first picking*.—Aug. 23, 2010.

*Date of last picking*.—Aug. 31, 2010, varies slightly with climatic conditions.

*Size*.—Medium. Average diameter axially 60.3 mm. Average transversely in suture plane 59.4 mm. Average weight 144.8 grams, average weight varies slightly with fertility of the soil, amount of thinning and climatic conditions.

*Form*.—Globose to slightly elongated.

*Suture*.—Nearly smooth to slightly lipped, extends from base to apex.

*Ventral surface*.—Very slightly lipped.

*Apex*.—Slightly retuse.

*Base*.—Varies from flat to slightly retuse.

*Stem cavity*.—Rounded to slightly elongated in the suture plane. Average depth 7.1 mm. Average diameter 2.7 mm.

Stem:

*Size*.—Small to medium. Average length 14.2 mm. Average diameter 2.5 mm.

*Color*.—Varies from 10YR 6/4 to 10YR 4/4.

Flesh:

*Ripens*.—Evenly.

*Texture*.—Crisp, meaty.

*Fibers*.—Few, small and tender.

*Firmness*.—Very firm, comparable to commercial varieties.

*Aroma*.—Moderate.

*Amydgalin*.—Undetected.

*Eating quality*.—Excellent.

*Flavor*.—Very sweet, a good balance between acid and sugar.

*Juice*.—Moderate amount, enhances flavor.

*Brix*.—Average Brix 26.0°, varies slightly with amount of fruit per tree and climatic conditions.

*Color*.—Varies from 2.5Y 8/6 to 2.5Y 8/10. Pit cavity varies from 7.5YR 5/8 to 10YR 6/8.

Skin:

*Thickness*.—Medium.

*Surface*.—Smooth.

*Bloom*.—Moderate amount, covers entire skin surface.

*Tendency to crack*.—Very slight with rain, varies with fruit maturity.

*Color*.—Ground color varies from 2.5Y 8/8 to 10YR 7/8. Partially overspread with 7.5R 3/8 to 10R 2/6.

*Tenacity*.—Tenacious to flesh.

*Astringency*.—Undetected.

Stone:

*Type*.—Clingstone.

*Size*.—Medium to large. Average length 28.2 mm. Average width 19.0 mm. Average thickness 8.8 mm.

*Form*.—Obovoid.

*Base*.—Flat.

*Apex*.—Slightly pointed. Average length 0.7 mm.

*Surface*.—Slightly pitted throughout.

*Sides*.—Unequal, one side extending further from the suture plane.

*Ridges*.—A small narrow ridge on each side of suture extending from base to apex.

*Tendency to split*.—None.

*Color*.—Varies from 7.5YR 5/6 to 7.5YR 4/6 when dry.

Kernel:

*Size*.—Medium. Average length 16.5 mm. Average width 9.2 mm. Average depth 4.6 mm.

*Form*.—Ovoid.

*Viability*.—Viable, complete embryo development.

*Skin color*.—7.5YR 4/6.

Use: Dessert.

*Market*.—Local and long distance.

Keeping quality: Good, held firm in cold storage 3 weeks at 38° to 42° F. without shriveling, internal breakdown of flesh or appreciable loss of eating quality.

Shipping quality: Good, showed minimal skin scarring or bruising during picking, packing or shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

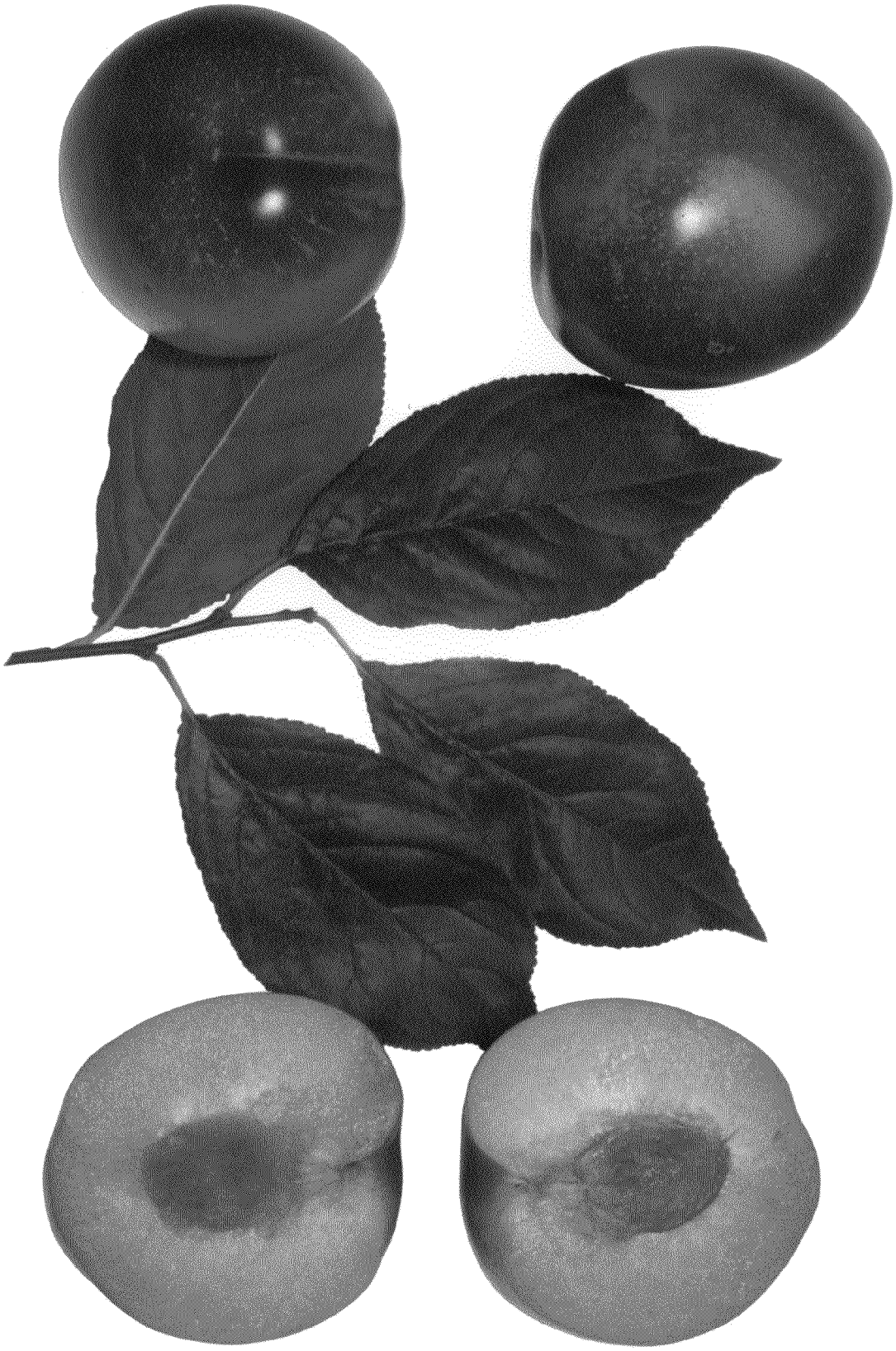

* * * * *